United States Patent
Kim et al.

(10) Patent No.: US 7,157,196 B2
(45) Date of Patent: Jan. 2, 2007

(54) NAPHTHALENETETRACARBOXYLIC ACID DIIMIDE DERIVATIVES AND ELECTROPHOTOGRAPHIC PHOTOCONDUCTIVE MATERIAL HAVING THE SAME

(75) Inventors: Seung-ju Kim, Suwon (KR); Saburo Yokota, Suwon (KR); Kyung-yol Yon, Seongnam (KR); Hwan-koo Lee, Suwon (KR); Beom-jun Kim, Seongnam (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 235 days.

(21) Appl. No.: 10/768,083

(22) Filed: Feb. 2, 2004

(65) Prior Publication Data

US 2005/0003286 A1 Jan. 6, 2005

(30) Foreign Application Priority Data

Jul. 4, 2003 (KR) ............... 10-2003-0045323

(51) Int. Cl.
*G03G 5/06* (2006.01)
(52) U.S. Cl. ............... 430/58.5; 430/78; 546/66
(58) Field of Classification Search ............... 546/66; 430/78, 58.5
See application file for complete search history.

(56) References Cited

U.S. PATENT DOCUMENTS

| | | | | |
|---|---|---|---|---|
| 1,935,945 | A | * | 11/1933 | Eckert et al. ............... 546/66 |
| 2,087,133 | A | * | 7/1937 | Vollmann ............... 546/66 |
| 3,931,224 | A | * | 1/1976 | Santa et al. ............... 546/66 |
| 4,442,193 | A | | 4/1984 | Chen et al. |
| 4,992,349 | A | * | 2/1991 | Chen et al. ............... 430/58.5 |
| 5,468,583 | A | | 11/1995 | Gruenbaum et al. |
| 5,541,169 | A | | 7/1996 | Deushi et al. |
| 5,558,965 | A | | 9/1996 | Nguyen et al. |

(Continued)

FOREIGN PATENT DOCUMENTS

JP 2000-147806 5/2000

(Continued)

OTHER PUBLICATIONS

Diamond, Arthur S & David Weiss (eds.) Handbook of Imaging Materials. New York: Marcel-Dekker, Inc. (Nov. 2001) pp. 381-382.*

(Continued)

*Primary Examiner*—Christopher Rodee
(74) *Attorney, Agent, or Firm*—Staas & Halsey LLP

(57) ABSTRACT

Naphthalenetetracarboxylic acid diimide derivatives include a structure represented by the following formula:

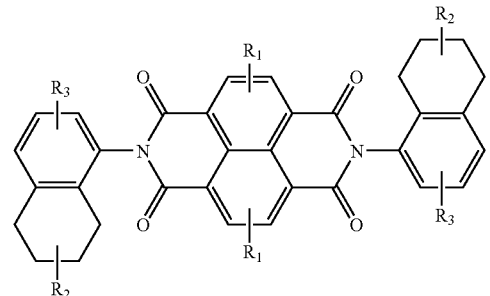

in which, $R_1$, $R_2$, and $R_3$ are each independently any one selected from the group consisting of hydrogen; halogen; substituted or unsubstituted alkyl of $C_1$ to $C_{20}$; substituted or unsubstituted alkoxy of $C_1$ to $C_{20}$; substituted or unsubstituted aryl of $C_6$ to $C_{30}$; and substituted or unsubstituted aralkyl of $C_7$ to $C_{30}$. An electrophotographic photoconductive material includes the naphthalenetetracarboxylic acid diimide derivatives as an electron transferring material.

11 Claims, 1 Drawing Sheet

U.S. PATENT DOCUMENTS

| | | | |
|---|---|---|---|
| 5,886,183 A * | 3/1999 | Langhals et al. | 546/62 |
| 6,287,736 B1 | 9/2001 | Takaki et al. | |
| 6,391,505 B1 * | 5/2002 | Hamasaki et al. | 430/78 |
| 6,472,514 B1 | 10/2002 | Kuroda | |
| 2003/0153005 A1 * | 8/2003 | Schmid et al. | 435/7.1 |
| 2005/0130051 A1 * | 6/2005 | Kim et al. | 430/60 |

FOREIGN PATENT DOCUMENTS

| | | |
|---|---|---|
| JP | 2003-030306 | 11/2000 |
| JP | 2001-066805 | 3/2001 |
| JP | 2003-029436 | 1/2003 |

OTHER PUBLICATIONS

Borsenberger, Paul M et al. Organic Photoreceptors for Imaging Systems. New York: Marcel-Dekker, Inc. (1993) pp. 356-361.*

* cited by examiner

NAPHTHALENETETRACARBOXYLIC ACID DIIMIDE DERIVATIVES AND ELECTROPHOTOGRAPHIC PHOTOCONDUCTIVE MATERIAL HAVING THE SAME

CROSS-REFERENCE TO RELATED APPLICATION

This application claims the benefit of Korean Patent Application No. 2003-45323 filed Jul. 4, 2003 in the Korean Intellectual Property Office, the disclosure of which is incorporated herein by reference.

BACKGROUND OF THE INVENTION

1. Field of the Invention

The present invention relates to naphthalenetetracarboxylic acid diimide derivatives and an electrophotographic photoconductive material comprising the same. More particularly, it relates to naphthalenetetracarboxylic acid diimide derivatives comprising a specific substituent and an electrophotographic photoconductive material having improved electron transporting ability by using the same as an electron transferring material.

2. Description of the Related Art

In an electrophotographic image forming apparatus, a photoconductive material is electrically charged and exposed to an image forming light source to form an electrostatic latent image. Next, the latent image is developed by a toner by applying a development voltage. The developed toner image is transferred to a recording medium such as paper, followed by fixation of the transferred image. Such electrophotography is widely used in various apparatuses such as digital or analog copying machines, printers, facsimiles, etc.

As a photoconductive material of the electrophotographic image forming apparatus, selenium photoconductive materials, amorphous silicone photoconductive materials, etc., were used in the past. However, organic photoconductive materials are widely used now. The organic photoconductive materials are classified into a multi-layered photoconductive material and single-layer photoconductor material. In the multilayered photoconductive material, a charge generating material (CGM) and a charge transferring material (CTM) are separately distributed into different layers of a layered laminate and perform different functions. In the single-layer photoconductive material, a charge generating material (CGM) and a charge transferring material (CTM) are dispersed in a single layer. The multi-layered photoconductive material is mainly used to produce a (−)type organic photoconductive material. The single-layer photoconductive material is mainly used to produce (+)type organic photoconductive material.

The (+)type single-layer organic photoconductive material has advantages in that it generates less ozone, which is harmful to human bodies, and it can be produced at a relatively low production cost since it has a single layer structure. In the (+)type organic photoconductive material, a photosensitive layer comprises an electron transferring material, a hole transferring material, a binder resin and a charge generating material. Since the electron transferring ability of the common electron transferring materials presently used is 100 times less than the hole transferring ability of the hole transferring material, the performance of the organic photoconductive material is largely affected by the electron transferring ability of the electron transferring material. Therefore, among the components contained in the photosensitive layer of the (+)type organic photoconductive material, the electron transferring material is the most important.

Examples of compounds commonly used as the electron transferring material include dicyanofluorenone, 2-nitro-9-fluorenone, 2,7-dinitro-9-fluorenone, 2,4,7-trinitro-9-fluorenone, 2,4,5,7-tetranitro-9-fluorenone, 2-nitrobenzothiopene, 2,4,8-trinitrothioxanthrone, dinitroanthracene, dinitroacridine, dinitroanthraquinone, naphthoquinone and 3,5-dimethyl-3'5'-di-t-butyldiphenoquinone. Since the compounds having the dicyanofluorenone and diphenoquinone structures have a weak electron transferring ability, when an organic photoconductive material is produced using these compounds as an electron transferring material, there are problems such as reduction in the charged potential and increase in the exposure potential upon use of a long period of time.

The electron transferring material having the naphthalenetetracarboxylic acid diimide structure is known to have an electron transferring ability superior to the naphthoquinone structure. The electron transferring ability of the electron transferring material having the naphthalenetetracarboxylic acid diimide structure is largely affected by the solubility of the electron transferring material in an organic solvent and compatibility of the electron transferring material with a polymer binder resin.

U.S. Pat. No. 4,442,193 discloses a photoconductive material composition comprising a photoconductive substance and a 1,4,5,8-naphthalenebisdicarboxylic acid diimide derivative compound. U.S. Pat. No. 5,468,583 discloses a photoconductive material comprising a conductive layer, a charge generating layer and a polymer binder having an electron transferring material dispersed therein. The electron transferring material comprises at least one of cyclic bisdicarboxylic acid imide compounds represented by formula 1:

FORMULA 1

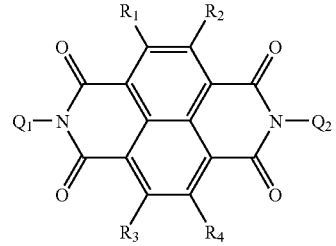

In formula 1, $Q_1$ and $Q_2$ are independently branched chain alkyl, un-substituted straight chain alkyl, unsubstituted cycloalkyl, alkyl-substituted cycloalkyl, unsubstituted straight-chain unsaturated alkyl, aryl, $C_2$ to $C_{20}$ alkyl, alkoxy or hydrogen, provided that both $Q_1$ and $Q_2$ are not hydrogen, $R_1$, $R_2$, $R_3$ and $R_4$ are, independently, hydrogen, $C_2$ to $C_4$ alkyl, a $C_2$ to $C_4$ alkoxy or halogen.

All of the electron transferring materials disclosed in the above patent comprise naphthalenetetracarboxylic acid diimide derivatives as an electron transferring material. The naphthalenetetracarboxylic acid diimide derivatives are the most expected compounds as an electron transferring material owing to their electron transferring abilities. However, the naphthalenetetracarboxylic acid diimide derivatives known so far are not sufficiently satisfactory in solubility to an organic solvent and compatibility with a binder resin. Also, since the derivatives are apt to crystallize and form precipitates in a photosensitive layer and an electron transferring layer, electrophotographic properties of the photoconductive material may deteriorate.

Meanwhile, when naphthalenetetracarboxylic acid diimide derivative compounds are used in a concentration which can maintain compatibility with the binder resin, the photoconductivity of the photoconductive material may deteriorate.

SUMMARY OF THE INVENTION

The present invention has been made to solve the above and/or other problems and thus, one aspect of the present invention is to provide naphthalenetetracarboxylic acid diimide derivative compounds with improved electron transferring ability.

It is another aspect of the present invention to provide an electrophotographic photoconductive material using a novel naphthalenetetracarboxylic acid diimide derivative compound having high solubility in an organic solvent, excellent compatibility with a binder resin and improved electron transferring ability as an electron transferring material.

Additional aspects and/or advantages of the invention will be set forth in part in the description which follows and, in part, will be obvious from the description, or may be learned by practice of the invention.

According to an aspect of the invention, the naphthalenetetracarboxylic acid diimide derivatives are represented by formula 2:

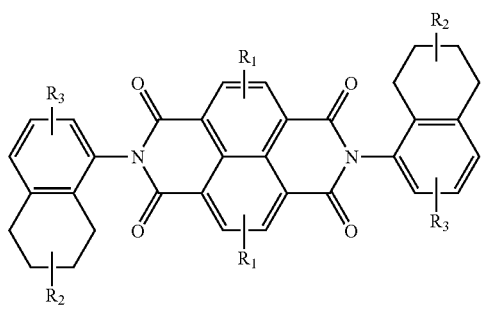

FORMULA 2 in which, $R_1$, $R_2$, and $R_3$ are, independently, any one selected from the group consisting of hydrogen, halogen, substituted or unsubstituted alkyl of $C_1$ to $C_{20}$, substituted or unsubstituted alkoxy of $C_1$ to $C_{20}$, substituted or unsubstituted aryl of $C_6$ to $C_{30}$, and substituted or unsubstituted aralkyl of $C_7$ to $C_{30}$.

According to an aspect of the invention, the substituted alkyl, substituted alkoxy and substituted aralkyl independently substituted with any one selected from the group consisting of alkyl, aryl, halogen and alkoxy.

According to an aspect of the invention, the substituted aryl is substituted with any one selected from the group consisting of alkyl, alkoxy, nitro and halogen.

According to another aspect of the invention, the electrophotographic photoconductive material comprises a substrate and a photosensitive layer formed on the substrate, in which the photosensitive layer comprises a charge generating material and a charge transferring material, and the charge transferring material comprises an electron transferring material comprising a naphthalenetetracarboxylic acid diimide derivative represented by formula 3:

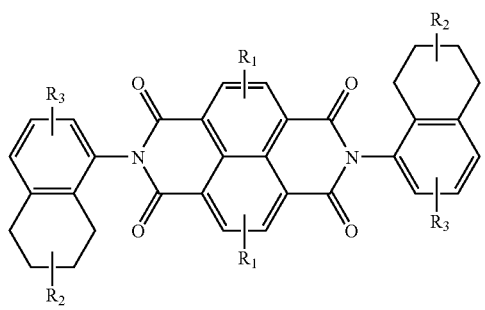

FORMULA 3 wherein, $R_1$, $R_2$, and $R_3$ are each independently any one selected from the group consisting of, hydrogen; halogen atom; substituted or unsubstituted alkyl of $C_1$ to $C_{20}$; substituted or unsubstituted alkoxy of $C_1$ to $C_{20}$; substituted or unsubstituted aryl of $C_6$ to $C_{30}$; and substituted or unsubstituted aralkyl of $C_7$ to $C_{30}$.

According to an aspect of the invention, the substituted alkyl, substituted alkoxy and substituted aralkyl are independently substituted with any one selected from the group consisting of alkyl, aryl, halogen and alkoxy.

According to an aspect of the invention, the substituted aryl is substituted with any one selected from the group consisting of alkyl, alkoxy, nitro and halogen.

According to an aspect of the invention, the electrophotographic photoconductive material contains the electron transferring material represented by formula 3 in a ratio of 20 wt % to 40 wt % based on the total solid components.

According to an aspect of the invention, the electrophotographic photoconductive material further comprises a hole transferring material.

According to an aspect of the invention, the photosensitive layer of the electrophotographic photoconductive material has a single-layer structure comprising the charge generating material and the charge transferring material dispersed in a binder resin.

According to an aspect of the invention, the photosensitive layer of the electrophotographic photoconductive material has a multi-layered structure comprising a charge generating layer comprising the charge generating material and a charge transferring layer comprising the charge transferring material.

According to an aspect of the invention, the electrophotographic photoconductive material further comprises an electron acceptor.

BRIEF DESCRIPTION OF THE DRAWINGS

The above aspects and features of the present invention will be more apparent by describing certain embodiments of the present invention with reference to the accompanying drawing, in which.

DETAILED DESCRIPTION OF THE EMBODIMENTS

Figure 1:
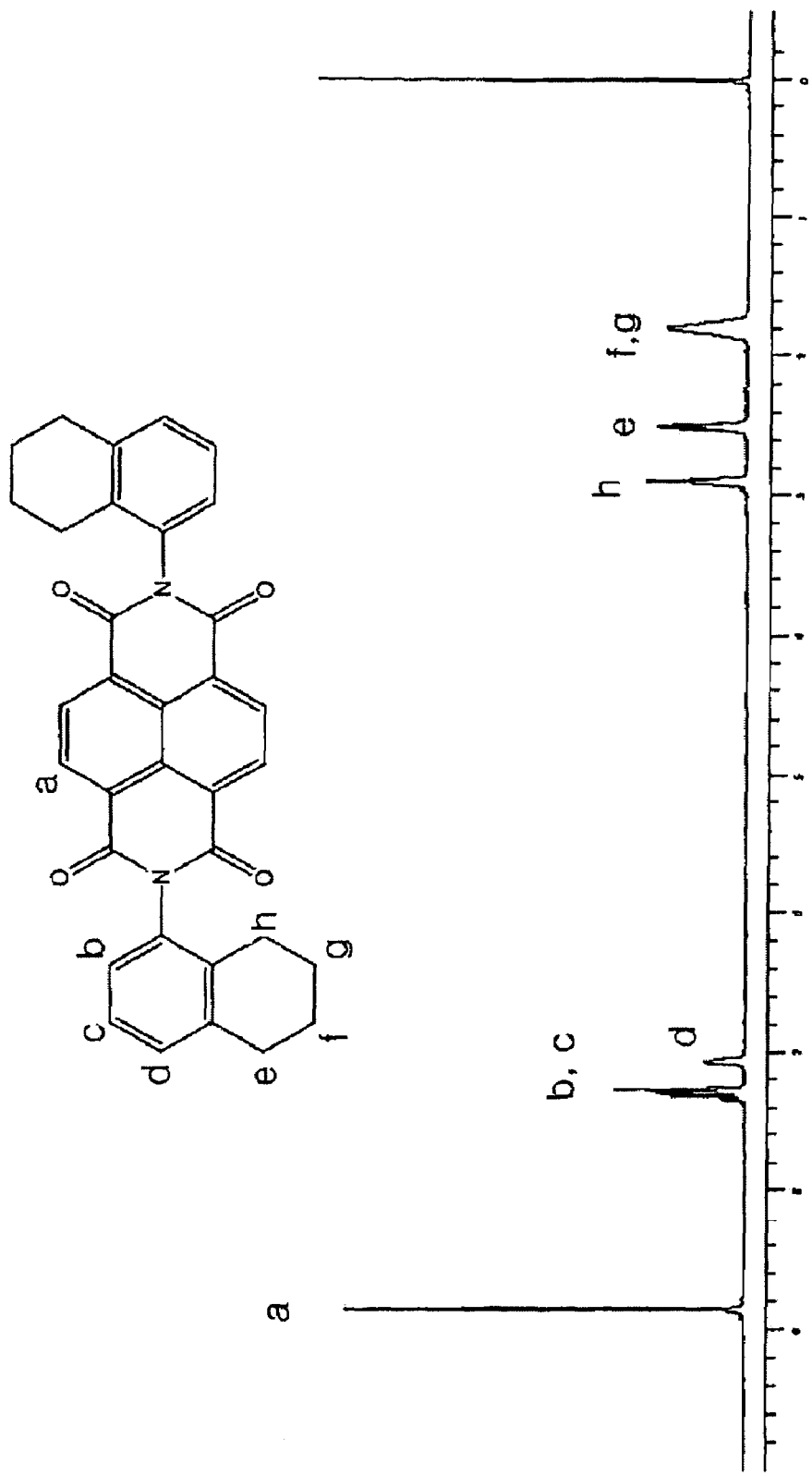
FIG. 1 is a graph showing NMR measured from a naphthalenetetracarboxylic acid diimide derivative compound according to an embodiment of the present invention.

Reference will now be made in detail to the embodiments of the present invention, examples of which are set forth below. The embodiments are described below to explain the present invention by referring to the examples.

The naphthalenetetracarboxylic acid diimide derivatives according to an aspect of the present invention represented by formula 2 as follows:

FORMULA 2

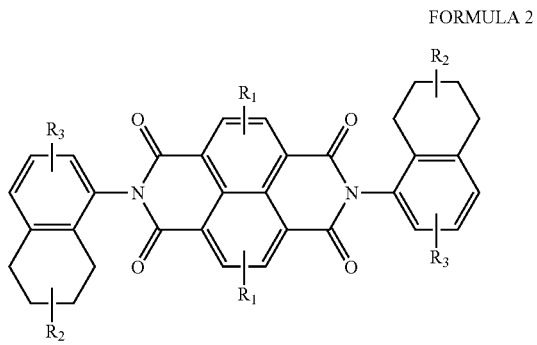

in which, $R_1$, $R_2$, and $R_3$ are, independently, any one selected from the group consisting of hydrogen, halogen, substituted or unsubstituted alkyl of $C_1$ to $C_{20}$, substituted or unsubstituted alkoxy of $C_1$ to $C_{20}$, substituted or unsubstituted aryl of $C_6$ to $C_{30}$, and substituted or unsubstituted aralkyl of $C_7$ to $C_{30}$.

The naphthalenetetracarboxylic acid diimide derivatives of formula 2 have a tetrahydronaphthalene structure attached to nitrogen atoms at both ends of a naphthalene-1,4,5,8-tetracarboxylic acid diimide structure. Referring to the Examples described below, the naphthalenetetracarboxylic acid diimide derivatives containing the tetrahydronaphthalene group may be synthesized.

The naphthalenetetracarboxylic acid diimide derivatives have a structural represented by the formula 2. In the derivatives, $R_1$, $R_2$, and $R_3$ are each independently any one selected from the group consisting of hydrogen, halogen, substituted or unsubstituted alkyl of $C_1$ to $C_{20}$, substituted or unsubstituted alkoxy of $C_1$ to $C_{20}$, substituted or unsubstituted aryl of $C_6$ to $C_{30}$, and substituted or unsubstituted aralkyl of $C_7$ to $C_{30}$.

In formula 2, where $R_1$, $R_2$, and $R_3$ are alkyl groups according to an aspect of the invention, the alkyl groups are $C_1$ to $C_{20}$ straight or branched alkyl groups according to aspects of the invention. Particularly, $C_1$ to $C_{12}$ straight or branched alkyl groups are preferred, although not required. A usable alkyl group includes, for example, methyl, ethyl, n-propyl, isopropyl, n-butyl, isobutyl, sec-butyl, t-butyl, pentyl, hexyl, 1,2-dimethyl-propyl, 2-ethyl-hexyl and the like, but are not limited thereto.

In formula 2, where $R_1$, $R_2$, and $R_3$ are alkoxy groups, the alkoxy groups are $C_1$ to $C_{20}$ alkoxy groups according to aspects of the invention. A usable alkoxy group includes methoxy, ethoxy, propoxy, phtoxy, pentyloxy and the like, but are not limited thereto.

In formula 2, where $R_1$, $R_2$, and $R_3$ are aryl groups, the aryl groups are $C_6$ to $C_{30}$ aryl groups according to aspects of the invention. Examples of usable aryl group include phenyl, tolyl, biphenyl, o-terphenyl, naphthyl, anthryl, phenanthryl and the like, but are not limited thereto.

In formula 2, where $R_1$, $R_2$, and $R_3$ are aralkyl groups, the aralkyl groups are $C_7$ to $C_{30}$ aralkyl groups according to aspects of the invention. The term "aralkyl group" used herein refers collectively to complex groups having a formula of $Ar(CH_2)_n$—, which are formed by substitution of an aromatic hydrocarbon group (aryl group), such as phenyl, tolyl and the like, at a carbon atom of an alkyl group, and is an abbreviation for the arylalkyl group. A usable aralkyl group includes, for example, benzyl($C_6H_5CH_2$—), phenethyl($C_6H_5CH_2CH_2$—), and the like, but are not limited thereto.

The alkyl group, alkoxy group and aralkyl group may independently have a substituent of alkyl such as methyl, ethyl, n-propyl, isopropyl, n-butyl, isobutyl, sec-butyl, t-butyl, pentyl, hexyl, 1,2-dimethyl-propyl and 2-ethyl-hexyl; halogen such as fluorine, chlorine, bromine and iodine; aryl such as phenyl, tolyl, biphenyl, o-terphenyl, naphthyl, anthryl and phenanthryl; or alkoxy such as or methoxy, ethoxy, propoxy, phtoxy and pentyloxy, but the usable substituent is not limited thereto.

The aryl group may have a substituent of alkyl such as methyl, ethyl, n-propyl, isopropyl, n-butyl, isobutyl, sec-butyl, t-butyl, pentyl, hexyl, 1,2-dimethyl-propyl and 2-ethyl-hexyl; halogen such as fluorine, chlorine, bromine and iodine; nitro; or alkoxy such as methoxy, ethoxy, propoxy, phtoxy and pentyloxy; but the usable substituent is not limited thereto.

Examples of the naphthalenetetracarboxylic acid diimide derivatives according to aspects of the present invention as described above are as follows, but are not limited thereto, in relation to formulas 4 through 10

FORMULA 4

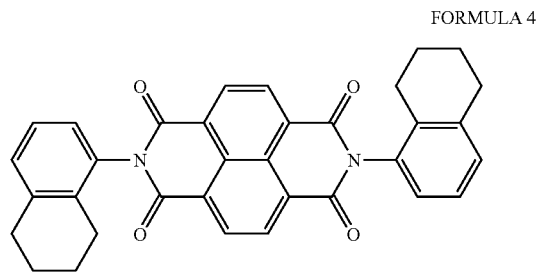

FORMULA 5

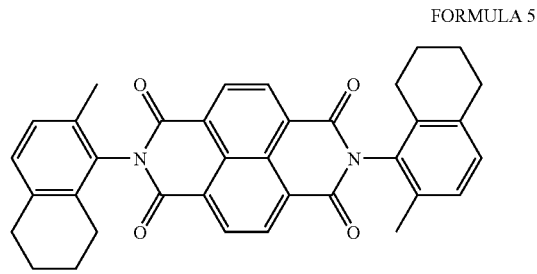

FORMULA 6

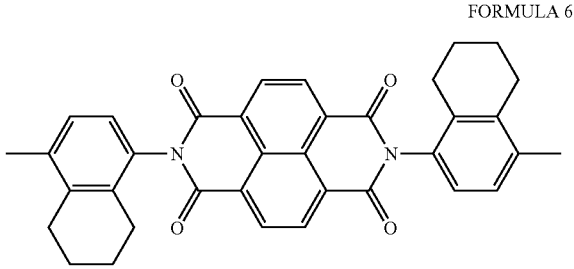

-continued

FORMULA 7

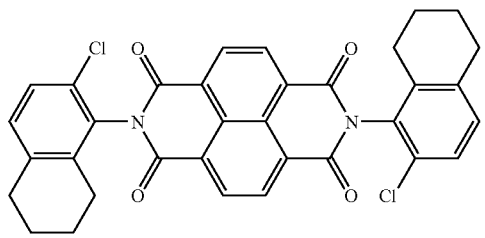

FORMULA 8

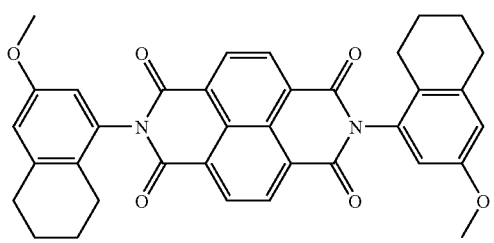

FORMULA 9

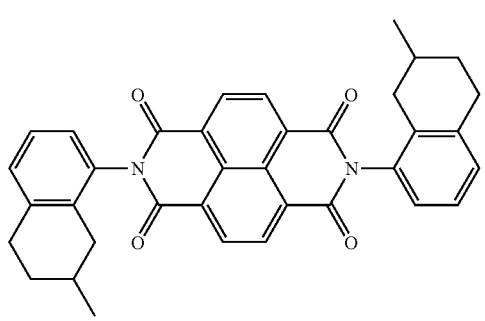

FORMULA 10

In order to synthesize the naphthalenetetracarboxylic acid diimide derivative of formula 2, amino-tetrahydronaphthalene(amino-tetrahydronaphthalene) is reacted with naphthalenetetracarboxilyic dianhydride according to an aspect of the invention.

A representative reaction scheme for synthesis of the naphthalenetetracarboxylic acid diimide derivative according to the present invention is shown as follows in relation to Reaction Scheme 1.

Reaction Scheme 1

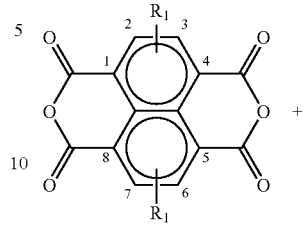

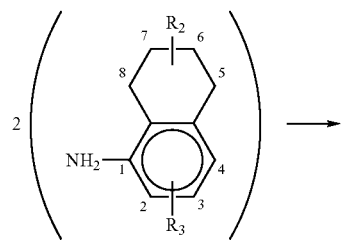

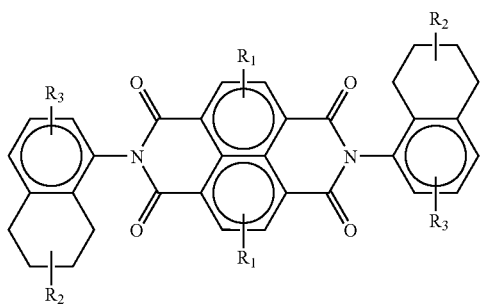

As shown in the Reaction Scheme 1, naphthalene-1,4,5,8-tetracarboxilic dianhydride may be reacted with 5,6,7,8-tetrahydro-1-naphthylamine to synthesize the naphthalene-tetracarboxylic acid diimide derivatives according to an aspect of the invention.

The electrophotographic photoconductive material according to an embodiment of the present invention may be prepared by the following embodiment.

The electrophotographic photoconductive material comprises a substrate and a photosensitive layer formed on the substrate, in which the photosensitive layer comprises a charge generating material and a charge transferring material.

The substrate should be made of a conductive material but is not required to be in all aspects of the invention. Examples of materials which can be used as the substrate include metals (such as aluminum, copper, tin, platinum, gold, silver, vanadium, molybdenum, chrome, cadmium, titanium, nickel, indium, stainless steel or brass), and plastics having the foregoing metals deposited or laminated thereon. Additional examples include glass coated with aluminum iodide, tin oxide or indium oxide. Particularly, an aluminum substrate is preferred according to an aspect of the invention.

The charge generating material contained in the photosensitive layer may be largely classified into an inorganic charge generating material and an organic charge generating material. The inorganic charge generating material may include, for example, zinc oxide, lead oxide and selenium. The organic charge generating material may include various pigment materials including phthalocyanine type pigments, various soluble organic compounds including organometals and polymeric organic charge generating materials.

Examples of the organic charge generating material include azo pigments, disazo pigments, anthanthrone pigments, phthalocyanine pigments, indigo pigments, threne pigments, toluidine pigments, pyrazoline pigments, phenylene pigments, quinacridone pigments and the like, which may be used alone or in combination. Particularly, phthalocyanine pigments, perylene pigments and bisazo pigments are preferably used, but other pigments are possible.

Examples of the phthalocyanine pigments include non-metal phthalocyanine, aluminum phthalocyanine, vanadium phthalocyanine, cadmium phthalocyanine, antimony phthalocyanine, chrome phthalocyanine, copper 4-phthalocyanine, germanium phthalocyanine, zinc phthalocyanine, chloroaluminum phthalocyanine, oxotitanyl phthalocyanine, chloroindium phthalocyanine, chlorogalium phthalocyanine, magnesium phthalocyanine, dialkyl phthalocyanine, tetramethyl phthalocyanine, and tetraphenyl phthalocyanine, but are not limited thereto.

The charge transferring material contained in the photosensitive layer may be largely classified into a hole transferring material and an electron transferring material. The charge transferring material which is used in the present invention is an electron transferring material, which is the naphthalenetetracarboxylic acid diimide derivatives, as described above.

The charge transferring material may further comprise a hole transferring material along with the electron transferring material. Examples of the hole transferring material include poly-N-vinylcarbazole, phenanthrene, N-ethylcarbazole, 2,5-diphenyl-1,3,4-oxadiazole, 2,5-bis-(4-diethylaminophenyl)-1,3,4-oxadiazole, bis-didiethylaminophenyl-1,3,6-oxadiazole, 4,4'-bis(diethylamino)-2,2'-dimethyltriphenylmethane, 2,4,5-triaminophenylimidazole, 2,5-bis(4-diethylaminophenyl)-1,3,4-triazole, 1-phenyl-3-(4-diethylaminostyryle)-5-(4-diethylaminophenyl)-2-pyrazoline, tetra(m-methylphenyl)methaphenylenediamine, N,N,N',N'-tetraphenylbenzidine derivatives, N,N'-diphenyl-N,N'-disilylbenzidine and the like, but are not limited thereto.

The charge generating material and the charge transferring material contained in the photosensitive layer are dispersed in the binder resin. Examples of the binder resin include styrene-butadiene copolymers, polyvinyl toluene-styrene copolymers, silicone resins, styrene alkyd resins, silicone-alkyd resins, soya-alkyd resins, poly(vinyl chloride), poly(vinylidene chloride), vinylidene chloride-acrylonitrile copolymers, poly(vinylacetate), vinyl acetate-vinylchloride copolymers, poly(vinylacetal) (such as poly(vinylbutyral)), polyacrylic- and methacrylic ester (such as poly(methylmethacrylate), poly(n-butylmethacrylate) and poly(isobutylmethacrylate)), polystyrene, nitrated polystyrene, polymethylstyrene, isobutylene polymers; polyester such as poly(4,4'-(2-norborvinylidene)bisphenylene azelate-co-terephthalate (60/40)) and poly(ethylene-co-alkylene-bis(alkylene-oxyaryl)-phenylenedicarboxylate); phenolformaldehyde resins, ketone resins, polyamides, polycarbonates, polythiocarbonates, poly(ethylene-co-isopropylidene-2,2-bis(ethyleneoxyphenylene)terephthalate); copolymers of vinylhaloarylate and vinyl acetate (such as poly(vinyl-m-bromobenzoate-co-vinyl acetate)); polyolefine (such as polyethylene chloride); and equivalents thereof. Particularly, polyester and polycarbonate are preferably used.

While not required in all aspects, a preferred electrophotographic photoconductive material contains the electron transferring material of formula 3 in a ratio of 20 wt % to 40 wt % based on a total weight of the solid components. If the content of the electron transferring material is less than 20 wt %, the electron transferring ability of the electron transferring material is deteriorated. If the content exceeds 40 wt %, the solubility of the electron transferring material in a solvent is lowered or the compatibility with a binder resin is deteriorated.

The photosensitive layer comprising the electron transferring material of formula 3 may be of a single layer structure or a laminate having a multi-layered structure.

The electrophotographic photoconductive material according to an aspect of the present invention may further comprise an electron acceptor in combination with the electron transferring material. Usable electron acceptors include, for example, benzoquinone type compounds such as (p-benzoquinone and 2,6-t-butylbenzoquinone), naphthoquinone type compounds (such as 1,4-naphthoquinone, 2-t-butyl-3-benzoyl-1,4-naphthoquinone and 2-phenyl-3-benzoyl-1,4-naphthoquinone), and diphenoquinone type compounds such as (3,5-dimethyl-3'5'-di-t-butyldiphenoquinone, 3,5-dimethoxy-3',5',di-t-butyldiphenoquinone, 3,3'-dimethyl-5,5'-di-t-butyldiphenoquinone, 3,5'-dimethyl-3'5-di-t-butyldiphenoquinone, 3,5,3',5'-tetramethyldiphenoquinone, 2,6,2',6'-tetra-t-butyldiphenoquinone, 3,5,3',5'-tetraphenyldiphenoquinone and 3,5,3',5'-tetraacyclohexyldiphenoquinone), but are not limited thereto.

The electrophotographic photoconductive material comprises, generally, a conductive substrate and a photosensitive layer formed on the substrate. The photosensitive layer is classified into a single-layer type photosensitive layer and a multi-layered type photosensitive layer according to the layer number in the photosensitive layer. Hence, the electrophotographic photoconductive material is also classified into a single-layer type electrophotographic photoconductive material and a multi-layered type electrophotographic photoconductive material. The single-layer type photosensitive layer and the multi-layered type photosensitive layer are differentiated according to whether the charge generating layer and the charge transferring layer play their roles without distinction in a single layer, or whether the layers are separated into different layers according to their roles, thereby forming a laminate. However, it should be understood that the lamination of a photosensitive layer on a conductive substrate to form a photoconductive material is identically applied to all the embodiments according to the present invention.

According to an aspect of the present invention, the lamination of the photosensitive layer on the substrate is performed by preparing a coating solution comprising the charge generating material and the charge transferring material, as described above, and coating the coating solution on a substrate. The coating solution is prepared using an organic solvent. Examples of organic solvents which can be used in the present invention include alcohols (such as methanol, ethanol, isopropanol and butanol), aliphatic hydrocarbon compounds (such as n-hexane, octane and cyclohexane), aromatic hydrocarbon compounds (such as benzene, toluene, and xylene), halogenated hydrocarbon compounds (such as dichloromethane, dichloroethane, carbon tetrachloride and chlorobenzene), ethers (such as dimethyl ether, diethyl ether, tetrahydrofuran, ethyleneglycol dimethyl ether and diethyleneglycol dimethyl ether), ketone compounds (such as acetone, methyl ethyl ketone and cyclohexane), ester compounds (such as ethyl acetate and methyl acetate), and dimethylformamide, dimethyl sulfoxide and the like, in which the set forth compounds may be used alone or in combination of two or more thereof.

When an aromatic is directly attached to an imide structure of the naphthalenetetracarboxylic acid diimide derivatives, the plane of benzene and the plane of naphthalene cross each other. Therefore, the two planes are oriented almost perpendicular to each other due to steric hinderance. That is, since the molecular structure of the naphthalenetetracarboxylic acid diimide derivative is not present in a single plane and hardly form an overlapped structure, the molecules are seldom crystallized with each other. However, though the crystallization between molecules is difficult, the coupling of naphthalenetetracarboxylic acid diimide derivative with the organic solvent molecule may become easy. Therefore, the solubility of the naphthalenetetracarboxylic acid diimide derivative to the organic solvent may increase.

Also, the tetrahydronaphthalene structure of the naphthalenetetracarboxylic acid diimide derivatives according to the present invention, which comprises benzene attached to an aliphatic cyclic compound, does not spatially form a plane but a zigzag line. For an aliphatic cyclic compound, a chair conformation, that is, a trans-type isomer, is 3-dimensionally stable. The aliphatic ring attached to benzene of the tetrahydronaphthalene structure according to the present invention has a zigzag folded conformation and thus, is structurally stable. Since the zigzag folded structure is asymmetric and the aliphatic cyclic compounds are structurally flexible, the coupling with the solvent molecule may be increased by the asymmetry and flexibility. Such ziazag folded molecular structure can be expected using CHEM3D ULTRA 6.0 program created by CAMBRIDGESOFT CORPORATION.

Therefore, the naphthalenetetracarboxylic acid diimide derivatives having the tetrahydronaphthalene structure according to the present invention have increased solubility in organic solvents and improved compatibility with binder resins.

Examples according to the present invention and effects thereof will be provided below. The below examples are provided by way of illustration of embodiments of the invention. It is understood that the scope of the invention is not limited to the detailed examples set forth below.

EXAMPLES

Synthesis of naphthalenetetracarboxylic acid diimide derivatives

Example 1

Reference was made to the Reaction Scheme 1.

10.72 g (0.04 mol) of naphthalene-1,4,5,8-tetracarboxylic acid dianhydride was mixed with 100 ml of dimethylformamide (DMF) at room temperature while stirring. To the stirred solution, a mixture of 12.37 g (0.084 mol) of 5,6,7,8-tetrahydro-1-naphthylamine and 20 ml of DMF was slowly added and stirred for 1 hour at room temperature. The reaction was refluxed for 3 hours while elevating the temperature, followed by cooling to room temperature.

To the cooled solution, 60 ml of methanol was added to form precipitates, followed by filtration. The filtered solids were recrystalized from a solvent mixture of chloroform and ethanol.

The recrystallized product was dried in vacuo to obtain 20.0 g of yellow crystals with a yield of 95%.

Preparation of electrophotographic photoconductive material

Example 2

| | |
|---|---|
| Electron transferring material of the formula 4: | 4.5 weight parts |
| α-type TiOPC of the following formula 11: | 0.9 weight parts |
| Hole transferring material of the following formula 12: | 9 weight parts |
| Binder resin of the following formula 13: | 15.9 weight parts |
| Methylene chloride: | 84 weight parts |
| 1,1,2-trichloroethane: | 36 weight parts |

The ingredients in the above weight ratio were sandmilled for 2 hours and dispersed by ultrasonic agitation. Then, the dispersion was coated on an aluminum-PET sheet by ring coating and dried at 110° C. for 1 hour. Thus, an electrophotographic photoconductive material having a thickness of about 12 μm was prepared.

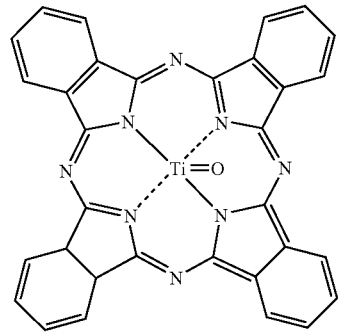

FORMULA 11

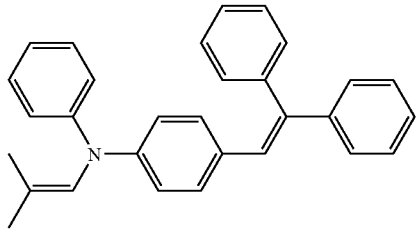

FORMULA 12

-continued

FORMULA 13

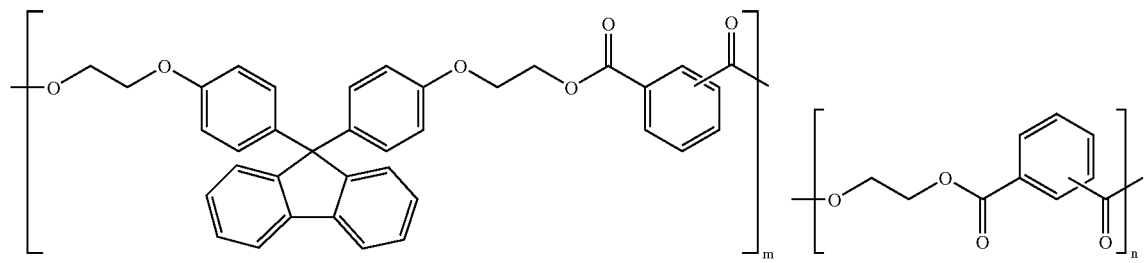

Example 3

| | |
|---|---|
| Electron transferring material of the formula 4: | 4.05 weight parts |
| α-type TiOPC of the formula 11: | 0.9 weight parts |
| Hole transferring material of the formula 12: | 9 weight parts |
| Binder resin of the formula 13: | 15.9 weight parts |
| Methylene chloride: | 84 weight parts |
| 1,1,2-trichloroethane: | 36 weight parts |
| Electron acceptor of the following formula 14: | 0.45 weight parts |

The ingredients in the above weight ratio were sandmilled for 2 hours and dispersed by ultrasonic agitation. Then, the dispersion was coated on an aluminum-PET sheet by ring coating and dried at 110° C. for 1 hour. Thus, an electrophotographic photoconductive material having a thickness of about 12 μm was prepared.

FORMULA 14

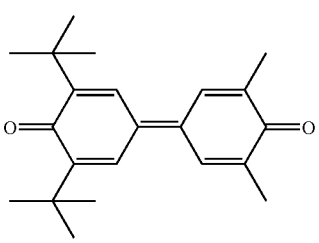

Comparative Example 1

| | |
|---|---|
| Electron transferring material of the following formula 15: | 4.5 weight parts |
| α-type TiOPC of the formula 11: | 0.9 weight parts |
| Hole transferring material of the formula 12: | 9 weight parts |
| Binder resin of the formula 13: | 15.9 weight parts |
| Methylene chloride: | 84 weight parts |
| 1,1,2-trichloroethane: | 36 weight parts |

The ingredients in the above weight ratio were sandmilled for 2 hours and dispersed by ultrasonic agitation. Then, the dispersion was coated on an aluminum-PET sheet by ring coating and dried at 110° C. for 1 hour.

FORMULA 15

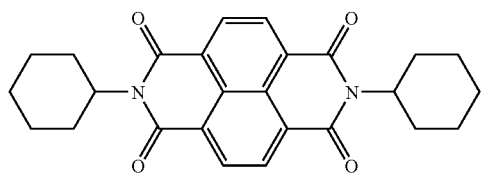

Comparative Example 2

| | |
|---|---|
| Electron transferring material of the formula 15: | 4.05 weight parts |
| ▼-type TiOPC of the formula 11: | 0.9 weight parts |
| Hole transferring material of the formula 12: | 9 weight parts |
| Binder resin of the formula 13: | 15.9 weight parts |
| Methylene chloride: | 84 weight parts |
| 1,1,2-trichloroethane: | 36 weight parts |
| Electron acceptor of the formula 14: | 0.45 weight parts |

The ingredients in the above weight ratio were sandmilled for 2 hours and dispersed by ultrasonic agitation. Then, the dispersion was coated on an aluminum-PET sheet by ring coating and dried at 110° C. for 1 hour.

Comparative Example 3

| | |
|---|---|
| Electron transferring material of the following formula 16: | 4.5 weight parts |
| α-type TiOPC of the formula 11: | 0.9 weight parts |
| Hole transferring material of the formula 12: | 9 weight parts |
| Binder resin of the formula 13: | 15.9 weight parts |
| Methylene chloride: | 84 weight parts |
| 1,1,2-trichloroethane: | 36 weight parts |

The ingredients in the above weight ratio were sandmilled for 2 hours and dispersed by ultrasonic agitation. Then, the dispersion was coated on an aluminum-PET sheet by ring coating and dried at 110° C. for 1 hour.

FORMULA 16

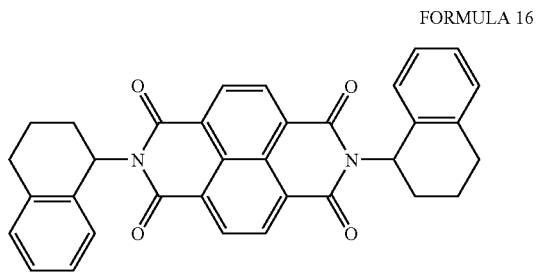

Comparative Example 4

| Electron transferring material of the formula 16: | 4.05 weight parts |
| α-type TiOPC of the formula 11: | 0.9 weight parts |
| Hole transferring material of the formula 12: | 9 weight parts |
| Binder resin of the formula 13: | 15.9 weight parts |
| Methylene chloride: | 84 weight parts |
| 1,1,2-trichloroethane: | 36 weight parts |
| Electron acceptor of the formula 14: | 0.45 weight parts |

The ingredients in the above weight ratio were sandmilled for 2 hours and dispersed by ultrasonic agitation. Then, the dispersion was coated on an aluminum-PET sheet by ring coating and dried at 110° C. for 1 hour.

Comparative Example 5

| α-type TiOPC of the formula 11: | 0.9 weight parts |
| Hole transferring material of the formula 12: | 13.5 weight parts |
| Binder resin of the formula 13: | 15.9 weight parts |
| Methylene chloride: | 84 weight parts |
| 1,1,2-trichloroethane: | 36 weight parts |

The ingredients in the above weight ratio were sandmilled for 2 hours and dispersed by ultrasonic agitation. Then, the dispersion was coated on an aluminum-PET sheet by ring coating and dried at 110° C. for 1 hour.

Comparative Example 6

| α-type TiOPC of the formula 11: | 0.9 weight parts |
| Hole transferring material of the formula 12: | 13.05 weight parts |
| Binder resin of the formula 13: | 15.9 weight parts |
| Methylene chloride: | 84 weight parts |
| 1,1,2-trichloroethane: | 36 weight parts |
| Electron acceptor of the formula 14: | 0.45 weight parts |

The ingredients in the above weight ratio were sandmilled for 2 hours and dispersed by ultrasonic agitation. Then, the dispersion was coated on an aluminum-PET sheet by ring coating and dried at 110° C. for 1 hour.

Potentials of the electrophotographic photoconductive material prepared in Example 2 to Comparative Example 6 are shown in Table 1 below.

TABLE 1

|  | $V_0$ | $V_d$ | $V_0$ 100 | $V_d$ 100 |
| --- | --- | --- | --- | --- |
| Example 2 | 470 | 91 | 470 | 92 |
| Example 3 | 487 | 91 | 489 | 94 |
| Comp. Example 1 | 477 | 107 | 415 | 97 |
| Comp. Example 2 | 481 | 105 | 438 | 100 |
| Comp. Example 3 | 444 | 101 | 397 | 93 |
| Comp. Example 4 | 490 | 96 | 452 | 92 |
| Comp. Example 5 | 485 | 112 | 440 | 104 |
| Comp. Example 6 | 494 | 113 | 448 | 102 |

In the table, $V_0$ represents initial charged potential, $V_d$ represents initial exposure potential, $V_0$ 100 represents charged potential after 100 cycles, and $V_d$ 100 represents exposure potential after 100 cycles.

As can be seen from Table 1, Example 2 and Example 3 showed lower initial exposure potentials as compared to Comparative Example 1 to Comparative Example 6. Therefore, it was noted that they are more efficient because electric power needed upon exposure is reduced. Also, in Example 2 and Example 3, it was shown that the charged potential and exposure potential after 100 cycles were similar to those at the initial stage without any significant difference, that is, the charged potential and exposure potential were maintained uniformly. However, in Comparative Examples 1 to 6, it was shown that the charged potential and exposure potential after 100 cycles were significantly lowered, as compared to those at the initial stage. Therefore, it was noted that the electrophotographic photoconductive material comprising the electron transferring material according to aspects of the present invention has excellent electron transferring ability and the electron transferring ability can be maintained for a long period of time.

As described above, according to an aspect of the present invention, it is possible to provide novel naphthalenetetracarboxylic acid diimide derivatives having increased solubility in organic solvents and improved compatibility with binder resins. Also, it is possible to produce an electrophotographic photoconductive material with excellent electron transferring ability by using the naphthalenetetracarboxylic acid diimide derivatives.

Although aspects of the present invention has been illustrated and explained in detail by embodiments described above, it should be understood that the present invention is not limited thereto, various modifications and changes can be made by those skilled in the art, without departing from the scope and spirit of the invention as disclosed in the accompanying claims and such modifications and changes fall in the scope of the present invention as defined in the claims and their equivalents.

What is claimed is:

1. A naphthalenetetracarboxylic acid diimide derivative represented by the following formula:

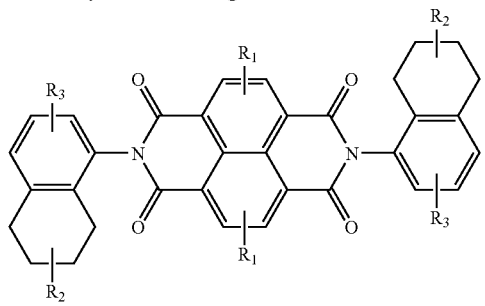

in which, $R_1$, $R_2$, and $R_3$ are each independently any one selected from the group consisting of hydrogen; halogen; substituted or unsubstituted alkyl of $C_1$ to $C_{20}$; substituted or unsubstituted alkoxy of $C_1$ to $C_{20}$; substituted or unsubstituted aryl of $C_6$ to $C_{30}$; and substituted or unsubstituted aralkyl of $C_7$ to $C_{30}$.

2. The naphthalenetetracarboxylic acid diimide derivative according to claim 1, wherein the substituted alkyl, substituted alkoxy and substituted aralkyl are independently substituted with any one selected from the group consisting of alkyl, aryl, halogen and alkoxy.

3. The naphthalenetetracarboxylic acid diimide derivative according to claim 1, wherein the substituted aryl is substituted with any one selected from the group consisting of alkyl, alkoxy, nitro and halogen.

4. An electrophotographic photoconductive material comprising a substrate and a photosensitive layer formed on the substrate, in which the photosensitive layer comprises a charge generating material and a charge transferring material, the charge transferring material is an electron transferring material and the electron transferring material comprises a naphthalenetetracarboxylic acid diimide derivative represented by the following formula:

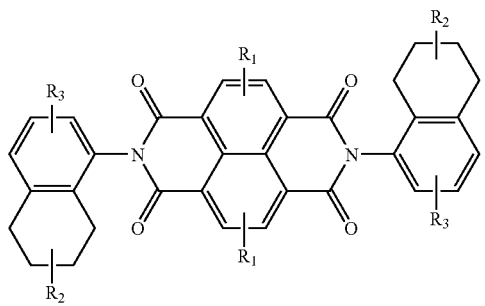

in which, $R_1$, $R_2$, and $R_3$ are each independently any one selected from the group consisting of hydrogen; halogen; substituted or unsubstituted alkyl of $C_1$ to $C_{20}$; substituted or unsubstituted alkoxy of $C_1$ to $C_{20}$; substituted or unsubstituted aryl of $C_6$ to $C_{30}$; and substituted or unsubstituted aralkyl of $C_7$ to $C_{30}$.

5. The electrophotographic photoconductive material according to claim 4, wherein the substituted alkyl, substituted alkoxy and substituted aralkyl are independently substituted with any one selected from the group consisting of alkyl, aryl, halogen and alkoxy.

6. The electrophotographic photoconductive material according to claim 4, wherein the substituted aryl is substituted with any one selected from the group consisting of alkyl, alkoxy, nitro and halogen.

7. The electrophotographic photoconductive material according to claim 4, wherein the electrophotographic photoconductive material contains the electron transferring material of the above formula in a ratio of 20 wt % to 40 wt % based on the total solid components.

8. The electrophotographic photoconductive material according to claim 4, wherein the electrophotographic photoconductive material further comprises a hole transferring material.

9. The electrophotographic photoconductive material according to claim 4, wherein the photosensitive layer has a single-layer structure comprising the charge generating material and the charge transferring material dispersed in an binder resin.

10. The electrophotographic photoconductive material according to claim 4, wherein the photosensitive layer has a layered structure comprising a charge generating layer comprising the charge generating material and a charge transferring layer comprising the charge transferring material.

11. The electrophotographic photoconductive material according to claim 4, wherein the electrophotographic photoconductive material further comprises an electron acceptor.

* * * * *